United States Patent
Gleiman et al.

(10) Patent No.: US 11,020,578 B2
(45) Date of Patent: Jun. 1, 2021

(54) SURGICAL STAPLER WITH INTEGRATED BLADDER

(71) Applicant: Covidien LP, Mansfield, MA (US)

(72) Inventors: Seth Gleiman, Guilford, CT (US); Anthony Ceniccola, Hamden, CT (US); Matthew Chowaniec, Madison, CT (US); David Racenet, Killingworth, CT (US); Gerald Hodgkinson, Guilford, CT (US); Joshua Snow, Clinton, CT (US); Jeffrey Schmitt, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 802 days.

(21) Appl. No.: 15/092,720

(22) Filed: Apr. 7, 2016

(65) Prior Publication Data
US 2016/0296227 A1    Oct. 13, 2016

Related U.S. Application Data

(60) Provisional application No. 62/148,827, filed on Apr. 17, 2015, provisional application No. 62/145,930, filed on Apr. 10, 2015.

(51) Int. Cl.
*A61M 37/00*    (2006.01)
*A61B 17/115*    (2006.01)
(Continued)

(52) U.S. Cl.
CPC ....... *A61M 37/00* (2013.01); *A61B 17/00491* (2013.01); *A61B 17/07207* (2013.01);
(Continued)

(58) Field of Classification Search
CPC ........ A61B 17/068; A61B 2017/00884; A61B 2017/07271; A61B 2017/07214; A61B 2017/00893; A61M 37/00
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |

(Continued)

FOREIGN PATENT DOCUMENTS

| | | |
|---|---|---|
| DE | 19924311 A1 | 11/2000 |
| EP | 0 327 022 A2 | 8/1989 |

(Continued)

OTHER PUBLICATIONS

International Search Report dated Jul. 25, 2016, issued in PCT/US2016/026334.

(Continued)

*Primary Examiner* — Anna K Kinsaul
*Assistant Examiner* — Daniel Jeremy Leeds
(74) *Attorney, Agent, or Firm* — Carter DeLuca & Farrell LLP (57) ABSTRACT

An end effector includes first and second members that each have a tissue contacting surface and are moveable relative to one another. The first and second members are configured to clamp tissue therebetween when in an approximated configuration. The tissue contacting surface of the first member defines a first groove. The end effector also includes a bladder that is defined within the first groove and is configured to receive and retain fluid.

19 Claims, 9 Drawing Sheets

(51) Int. Cl.
*A61B 17/00* (2006.01)
*A61B 17/072* (2006.01)

(52) U.S. Cl.
CPC . *A61B 17/1155* (2013.01); *A61B 2017/00884* (2013.01); *A61B 2017/00893* (2013.01); *A61B 2017/07214* (2013.01); *A61B 2017/07271* (2013.01)

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |

(56) References Cited

U.S. PATENT DOCUMENTS

| | | | |
|---|---|---|---|
| 6,953,139 B2 | 10/2005 | Milliman et al. |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess |
| 7,455,682 B2 | 11/2008 | Viola |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,783 B2 * | 3/2010 | Morgan ........... A61B 17/07207 227/180.1 |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 * | 12/2010 | Viola ............... A61B 17/00491 227/179.1 |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,292,154 B2 | 10/2012 | Marczyk |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 * | 3/2014 | Viola ............... A61B 17/07207 227/175.1 |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |

(56) References Cited

U.S. PATENT DOCUMENTS

| | | |
|---|---|---|
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,375,259 B2 * | 6/2016 | Payne ................ A61B 18/1445 |
| 9,895,147 B2 * | 2/2018 | Shelton, IV ..... A61B 17/07207 |
| 10,130,359 B2 * | 11/2018 | Hess ....................... F16B 15/00 |
| 2002/0028243 A1 | 3/2002 | Masters |
| 2002/0086990 A1 | 7/2002 | Kumar et al. |
| 2002/0091397 A1 | 7/2002 | Chen |
| 2003/0065345 A1 | 4/2003 | Neadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0093029 A1 | 5/2004 | Zubik et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0143756 A1 | 6/2005 | Jankowski |
| 2005/0145671 A1 * | 7/2005 | Viola ................ A61B 17/00491 227/175.1 |
| 2005/0149073 A1 | 7/2005 | Arani et al. |
| 2005/0154093 A1 | 7/2005 | Kwon et al. |
| 2006/0004407 A1 | 1/2006 | Hiles et al. |
| 2006/0008505 A1 | 1/2006 | Brandon |
| 2006/0093672 A1 | 5/2006 | Kumar et al. |
| 2006/0111738 A1 * | 5/2006 | Wenchell ......... A61B 17/00491 606/186 |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0073340 A1 | 3/2007 | Shelton et al. |
| 2007/0114262 A1 | 5/2007 | Mastri et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 * | 5/2008 | Orban ................... A61B 17/115 227/176.1 |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 * | 5/2009 | Murray ............ A61B 17/00491 227/180.1 |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016888 A1 | 1/2010 | Calabrese et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0204641 A1 | 8/2010 | Wenchell |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0278346 A1 * | 11/2011 | Hull ................. A61B 17/00491 227/180.1 |
| 2011/0293690 A1 | 12/2011 | Griffin et al. |
| 2012/0018487 A1 | 1/2012 | Bettuchi et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0150221 A1 | 6/2012 | Viola |

(56) References Cited

U.S. PATENT DOCUMENTS

| | | |
|---|---|---|
| 2012/0187179 A1 | 7/2012 | Gleiman |
| 2012/0197272 A1 | 8/2012 | Oray et al. |
| 2012/0241492 A1* | 9/2012 | Shelton, IV ......... H05K 999/99 |
| | | 227/175.1 |
| 2012/0241499 A1 | 9/2012 | Baxter, III et al. |
| 2012/0273547 A1 | 11/2012 | Hodgkinson et al. |
| 2013/0032626 A1 | 2/2013 | Smith et al. |
| 2013/0037596 A1 | 2/2013 | Bear et al. |
| 2013/0062391 A1* | 3/2013 | Boudreaux ...... A61B 17/00491 |
| | | 227/175.1 |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze |
| 2013/0193186 A1 | 8/2013 | (Tarinelli) Racenet et al. |
| 2013/0193192 A1 | 8/2013 | Casasanta, Jr. et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0097224 A1 | 4/2014 | Prior |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115014 A1* | 4/2015 | Matonick ............ A61B 17/1155 |
| | | 227/175.1 |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2016/0206864 A1* | 7/2016 | Matonick ............. A61B 17/072 |
| 2016/0206865 A1* | 7/2016 | Matonick .......... A61M 37/0015 |

FOREIGN PATENT DOCUMENTS

| | | |
|---|---|---|
| EP | 0 594 148 A1 | 4/1994 |
| JP | H06327684 A | 11/1994 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 2006044799 A2 | 4/2006 |
| WO | 2010075298 A2 | 7/2010 |

OTHER PUBLICATIONS

Extended European Search Report dated Jan. 15, 2019 issued in corresponding EP Appln. No. 16777239.1.

Australian Office Action issued in Application No. 2016246716 dated Nov. 21, 2019.

Australian Office Action issued in Application No. 2016246716, dated Apr. 14, 2020.

Extended European Search Report issued in EP Application No. EP16777239.1, dated Jan. 15, 2019.

\* cited by examiner

SURGICAL STAPLER WITH INTEGRATED BLADDER

CROSS-REFERENCE TO RELATED APPLICATIONS

This application claims the benefit of and priority to U.S. Provisional Patent Application Ser. No. 62/148,827 filed Apr. 17, 2015, this application also claims the benefit of and priority to U.S. Provisional Patent Application Ser. No. 62/145,930 filed Apr. 10, 2015, the entire disclosure of which is incorporated by reference herein.

BACKGROUND

1. Technical Field

The present disclosure relates to surgical instruments and, more specifically, to surgical instruments with integrated bladders.

2. Discussion of Related Art

Throughout the years the medical field has utilized various techniques in an effort to join or bond body tissue together. Surgical staplers have been developed for joining adjacent tissue, for providing hemostasis of adjacent tissue, and for providing hemostasis in conjunction with cutting of adjacent tissue. Such surgical staplers include both linear and annular type configurations. The intended function of staples is to hold the edges of a wound or tissue against one another during the healing process so as to reduce discomfort, pain, scarring and the time required for healing.

Linear or annular surgical stapling devices are employed by surgeons to sequentially or simultaneously apply one or more rows of surgical fasteners, e.g., staples or two-part fasteners, to body tissue for the purpose of joining segments of body tissue together and/or for the creation of anastomoses. Linear surgical stapling devices generally include a pair of jaws between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples.

Annular surgical stapling devices generally include an annular staple cartridge assembly including a plurality of annular rows of staples, typically two rows of staples, an anvil assembly operatively associated with the annular cartridge assembly, and an annular blade disposed internal of the rows of staples.

In addition to the use of surgical staples, biological tissue adhesives have been developed for joining tissue. Generally, biological adhesives bond separated tissues together. Such adhesives may be used instead of suturing and stapling, for example, in surgical procedures, for the repair of tissue or the creation of anastomoses.

In addition to the use of biological adhesives, following the formation of the anastomosis, a separate instrument or device may be used to apply biological sealants to the outer surface of the anastomosis, typically in a separate step. The biological sealants are intended to reduce and/or stop the incidence of leakage from the anastomosis.

The application of adhesives and/or sealants offers many advantages to the patient and the surgeon alike, such as, for example, the possible reduction in the number of staples used, immediate sealing of the tissue being treated, a strengthening of the anastomosis, minimizing foreign body reaction and scarring, and a reduction in the occurrence of bleeding from the blood vessels, leakage through the tissue joint, and stricture.

There remains room for improvement in the delivery of fluids, such as adhesives and/or sealants, from surgical stapling instruments.

SUMMARY

Surgical staplers in accordance with this disclosure include end effectors having integrated bladders which dispense fluid (e.g., therapeutic drug, sealant, adhesive, or medicant) when punctured by a fastener during the joining of tissue by the surgical stapler. The bladder may be prefilled with fluid or fluid may be injected into the bladder prior to or during a surgical procedure.

In an aspect of the present disclosure, an end effector includes first and second members that each have a tissue contacting surface and are moveable relative to one another. The first and second members are configured to clamp tissue therebetween when in an approximated configuration. The tissue contacting surface of the first member defines a first groove. The end effector also includes a bladder that is defined within the first groove and is configured to receive and retain fluid.

In aspects, the bladder is configured to receive a fluid when the first and second members are in the approximated position. The bladder may be defined by an inner surface of the first groove and a first film disposed on the tissue contacting surface of the first member.

In some aspects, the end effector includes an injection port that is in fluid communication with the bladder. The injection port may be located on one of the first or second members and is configured to receive fluid from an injection device while the first and second members are in the approximated configuration.

In certain aspects, the first member includes a fastener that is configured to pierce the bladder as the fastener is ejected from the first member. The bladder may be configured to dispense a fluid onto tissue adjacent or proximate to the tissue contacting surface of the first member when the fastener pierces the bladders.

In particular aspects, the tissue contacting surface of the second member defines a second groove. The end effector may include a second bladder defined by an inner surface of the second groove and a second film disposed on the tissue contacting surface of the second member.

In aspects, the end effector is an annular end effector with the first member being a shell assembly and the second member being an anvil assembly. Alternatively, the end effector is a linear end effector with the first member being a lower jaw and the second member being an upper jaw.

In another aspect of the present disclosure, a method of joining tissue includes approximating first and second members of an end effector to clamp tissue to be joined between the first and second members, injecting fluid into a bladder defined in one of the first or second members while the first and second members are clamped on tissue, and ejecting a fastener from the first member such that the fastener pierces the bladder to release fluid from the bladder.

In aspects, ejecting the fastener from the first member includes the fastener piercing the bladder before the fastener passes through the tissue to be joined and coating the fastener with fluid disposed within the bladder. Ejecting the fastener from the first member may include the fastener piercing the bladder after the fastener passes through the tissue to be joined such that the bladder secretes fluid on tissue adjacent a tissue contacting surface of the second member.

In some aspects, injecting fluid into a bladder includes injecting fluid that includes at least one of a therapeutic drug, a biocompatible adhesive, or a biocompatible sealant. Injecting fluid into a bladder may include injecting a first fluid into a bladder that is defined by the first member and injecting a second fluid into a bladder that is defined by the second member. The second fluid may be different from the first fluid.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of device or component thereof that is farthest from the clinician.

This disclosure is generally related to end effectors for surgical staplers including integrated bladders which disperse a fluid (e.g., therapeutic drug, sealant, adhesive, or medicant) when punctured by a fastener to assist in the joining of tissue with the surgical stapler. The bladder may be prefilled with the fluid during manufacture of the instrument or the fluid may be injected into the integrated bladder prior to or during a surgical procedure. The end effector may have an integrated bladder on each side of the tissue with the same or different fluid being dispensed from each integrated bladder. The end effector may be supplied as a part of a loading unit (disposable or reusable) or may be supplied as part of surgical instrument. The end effector may be linear or annular in configuration. In addition, the surgical stapler may be manually actuated, may be actuated by an electromechanical handle, or may be actuated by a pneumatic handle. For example, the pneumatic handle can be a handle powered by a gas cylinder.

Figure 1:
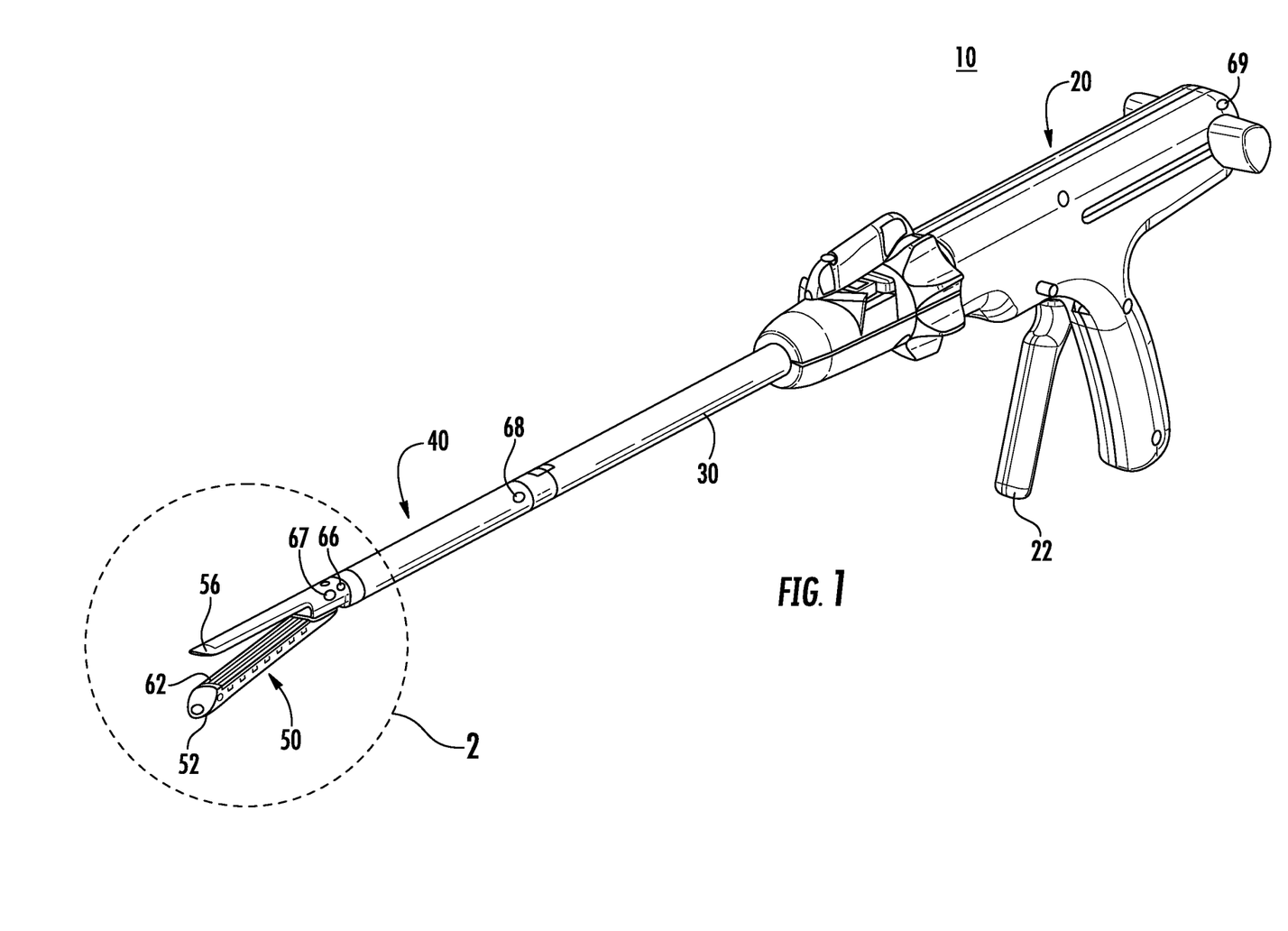
FIG. 1 is a perspective view of a surgical instrument with a manually actuated handle assembly and a linear stapling end effector in accordance with an exemplary embodiment of the present disclosure.

Referring now to FIG. 1, a surgical instrument 10 having a manually actuated handle assembly 20 including a linear stapling end effector 50 is provided in accordance with an exemplary embodiment of the present disclosure. The surgical instrument 10 includes the manually actuated handle assembly 20, an elongate portion 30, a loading unit 40, and an end effector 50. The elongate portion 30 extends from the handle assembly 20 and supports the loading unit 40. The loading unit 40 is releasably coupled to the distal end of the elongate portion 30. The end effector 50 is supported at a distal end of the loading unit 40 and includes first and second jaws 52, 56 that are moveable relative to one another. The handle assembly 20 includes a moveable handle 22 that is configured to actuate the end effector 50 to approximate the first and second jaws 52, 56 of the end effector 50 relative to one another and to fire or eject a plurality of fasteners (e.g., staples) through tissue positioned between the first and second jaws 52, 56. For a detailed description of a suitable manually actuated handle assembly and stapling instrument reference may be made to U.S. Pat. No. 8,789,737 ("the '737 Patent"), the entire contents of which is incorporated herein by reference.

Figure 2:
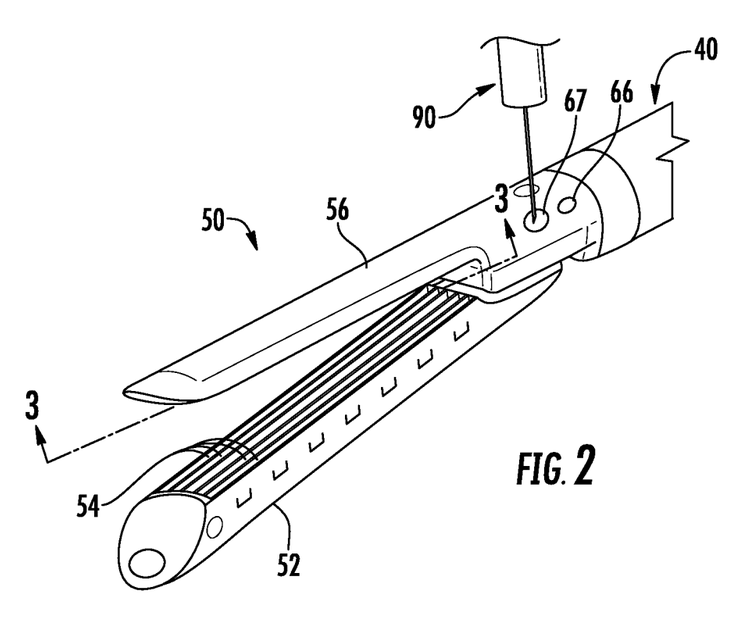
FIG. 2 is an enlarged view of the indicated area of detail of FIG. 1 with an injection device inserted into an injection port of the end effector.
Figure 3:
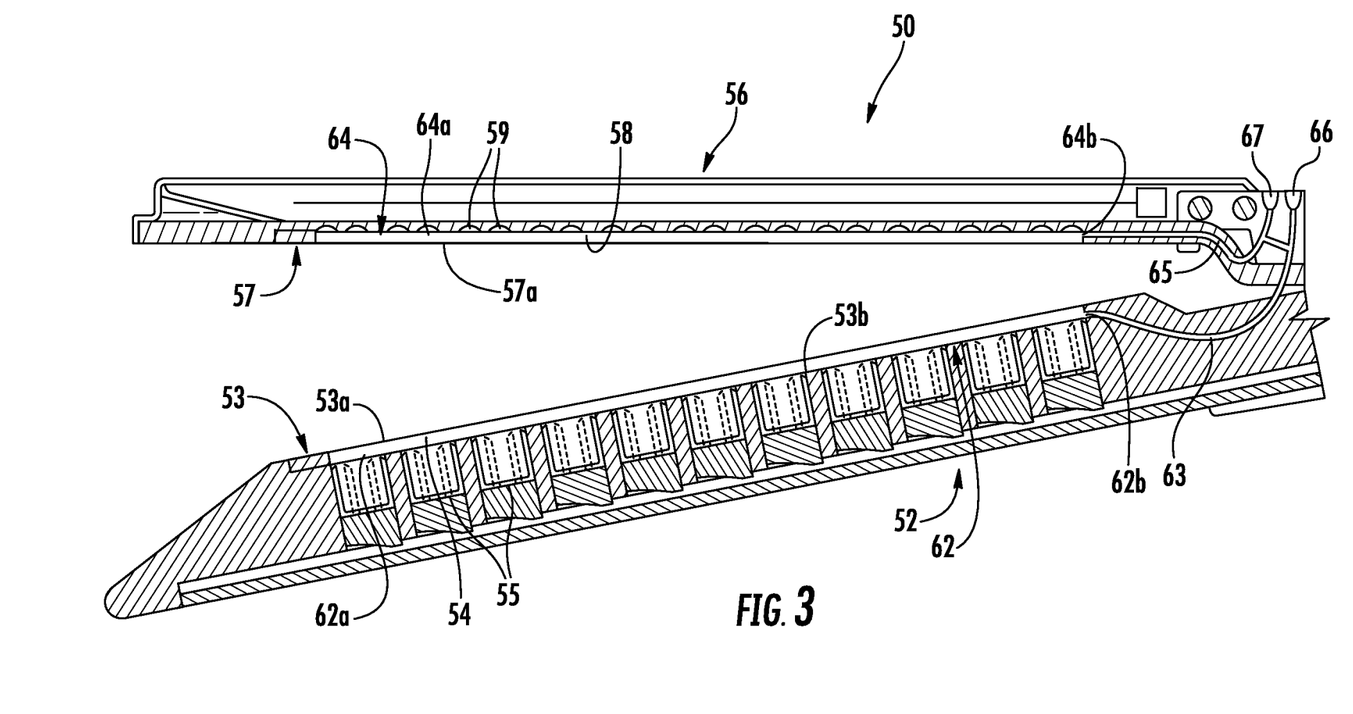
FIG. 3 is a cross-sectional view taken along the section line 3-3 of FIG. 2.

With reference to FIGS. 2 and 3, the first or lower jaw or member 52 of the end effector 50 includes a tissue contacting surface 53 that defines longitudinal grooves 54. Each of the grooves 54 includes an inner surface (in embodiments a pair of sidewalls and a bottom surface) and is positioned over a line of fasteners 55. The lower jaw 52 includes an integrated bladder 62 disposed within one or more of the grooves 54. The integrated bladder 62 is formed from an upper film 53a disposed along the tissue contacting surface 53 of the lower jaw 52 and a lower film 53b that is disposed over a bottom surface of the groove 54 such that sidewalls of the groove 54 form sidewalls of the integrated bladder 62. The upper film 53a may be disposed over the entire tissue contacting surface 53 of the lower jaw 52 and secured to the tissue contacting surface 53 between each of the grooves 54. The end effector 50 defines an injection port 66 and includes a delivery tube 63 that extends from the injection port 66, through the lower jaw 52, and to the integrated bladder 62 such that the injection port 66 is in fluid communication with the integrated bladder 62. The integrated bladder 62 may include fingers 62a with each finger 62a extending through a respective groove 54 and a plenum 62b in fluid communication with each finger 62a. The plenum 62b is in fluid communication with the injection port 66 through the delivery tube 63. Alternatively, the integrated bladder 62 may be formed from individual fingers 62a with the delivery tube 63 in fluid communication with each of the individual fingers 62a. The injection port 66 may include an auto-sealing septum to prevent injected fluid from exiting through the injection port 66.

It is also contemplated, that the integrated bladder 62 may be formed from individual fingers 62a with each finger 62a in fluid communication with the injection port 62 through an individual delivery tube 63 such that each individual delivery tube 63 is separately accessible through the injection port 66 to deliver a different fluid to each individual finger 62a. In such an embodiment, the individual fingers 62a may be paired with one or more delivery tubes 63 such that the inner fingers 62a of the integrated bladder 62 (adjacent a knife slot (not explicitly shown)) may be filled with a first fluid and the outer fingers 62a of the integrated bladder 62 (away from a knife slot (not explicitly shown)) may be filled with a second fluid that is different from the first fluid.

Further, it is contemplated that the second or upper jaw or member 56 may define longitudinal grooves 58 in a tissue contacting surface 57 of the upper jaw 56. Each of the grooves 58 is positioned over a line of staple pockets 59 or retainers (not shown). The upper jaw 56 includes an integrated bladder 64 that is disposed within each of the grooves 58 and a delivery tube 65 in fluid communication with the integrated bladder 64. The integrated bladder 64 is formed from a lower film 57a that is disposed along the tissue contacting surface 57 of the upper jaw 56 such that the staple pockets 59 and sidewalls defining the grooves 58 form the integrated bladder 64. The lower film 57a may be disposed over the entire tissue contacting surface of the upper jaw 56 and secured to the tissue contacting surface 57 between each of the grooves 58. The injection port 66 and the delivery tube 65 are also in fluid communication in a manner similar to the integrated bladder 62 and delivery tube 63 of the lower jaw 52. Similarly, the integrated bladder 64 may include fingers 64a with each finger 64a extending through a respective groove 58 and a plenum 64b in fluid communication with each finger 64a. The plenum 64b is in fluid communication with the injection port 66 through the delivery tube 65. Alternatively, the integrated bladder 64 may be formed from individual fingers 64a with the delivery tube 65 in fluid communication with each of the individual fingers 64a. In addition, the end effector 50 may define a second injection port 67 adjacent the injection port 66 which is in fluid communication with the integrated bladder 64. In such embodiments, the integrated bladder 64 of the upper jaw 56 is in fluid communication with the second injection port 67 and the integrated bladder 62 of the lower jaw 52 is in fluid communication with the injection port 66 such that each of the bladders 62, 64 may be individually and separately filled as detailed below. As shown, both injection ports 66, 67 are positioned on the upper jaw 56; however, it is contemplated that one or both of the injection ports 66, 67 may be positioned on the lower jaw 52.

Figure 4:
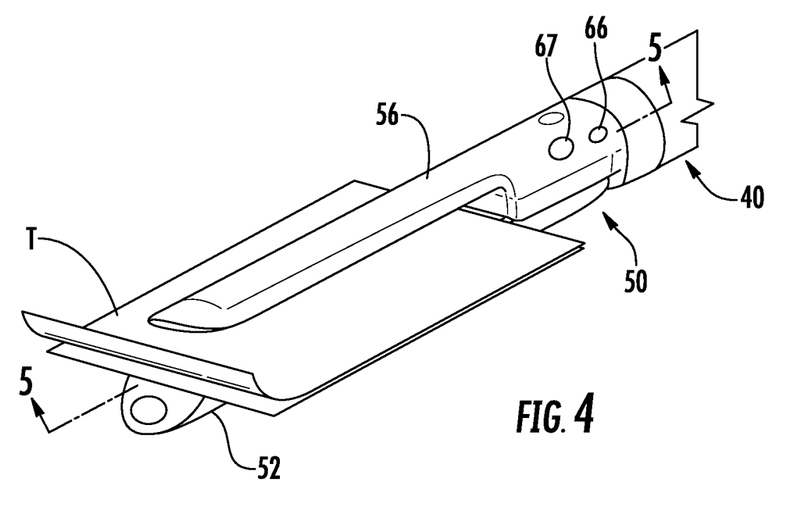
FIG. 4 is a perspective view of the end effector of FIG. 2 with jaws of the end effector approximated on tissue.
Figure 5:
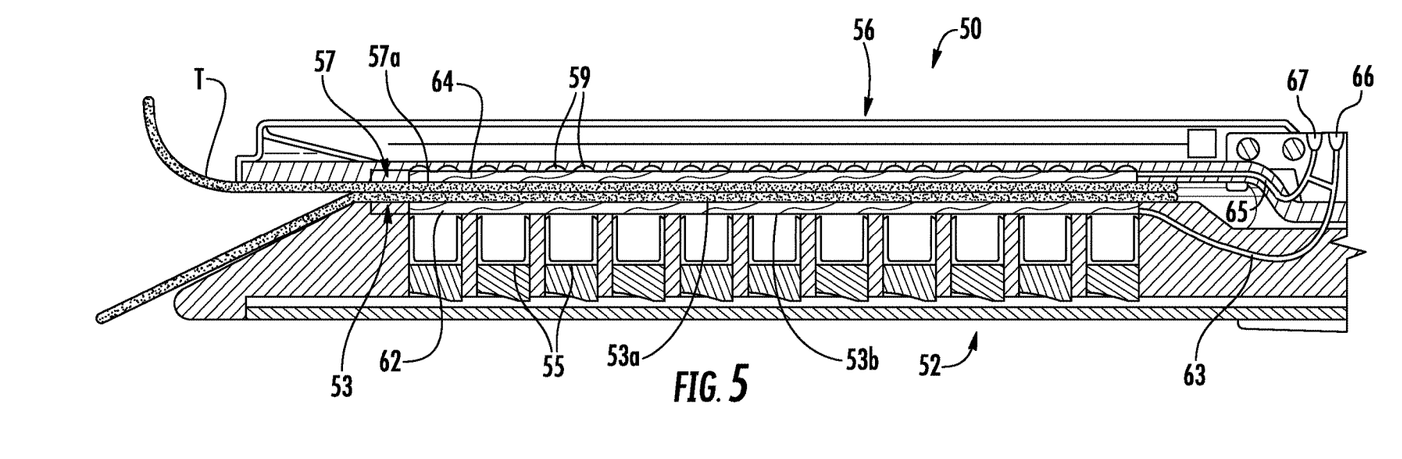
FIG. 5 is a cross-sectional view taken along the second line 5-5 of FIG. 4.

Referring now to FIGS. 2-5, the integrated bladder 62 has an initial or unfilled configuration (FIGS. 2 and 3) and a filled configuration (FIGS. 4 and 5). In the unfilled configuration, the integrated bladder 62 is collapsed such that an upper surface of the integrated bladder 62 is positioned below the tissue contacting surface 53 of the lower jaw 52. In the filled configuration, fluid which is injected through the injection port 66 fills or expands the integrated bladder 62 such that the upper surface of the integrated bladder 62 is coplanar with the tissue contacting surface 53 of the lower jaw 52. In addition, as the integrated bladder 62 is filled through the injection port 66, the integrated bladder 62 may expand to fill any cavities within the grooves 54. It is contemplated that the integrated bladder 62 may include semi-rigid walls such that in the unfilled configuration the upper surface of the integrated bladder 62 is coplanar with the tissue contacting surface 53 of the lower jaw 52.

With particular reference to FIG. 2, an injection device or needle 90 may be inserted into the injection port 66 to inject a fluid into the integrated bladder 62. The fluid may include a therapeutic drug, a biocompatible sealant, a biocompatible adhesive, or a combination thereof. The material can be a bioactive material such as a drug, an immunosuppressant, steroid, entihistimine, etc. Anti-adhesives, antimicrobials, anesthetics, growth factors, or other materials are contemplated.

As the fluid is injected into the integrated bladder 62, the integrated bladder 62 transitions to the filled configuration as detailed above. As the integrated bladder 62 reaches the filled configuration, the pressure of the fluid within the needle 90 may exceed a threshold pressure to indicate that the integrated bladder 62 is in the filled configuration. Additionally or alternatively, as the integrated bladder 62 reaches the filled configuration, the fluid may flow out of the injection port 66 to provide an indication that the integrated bladder 62 is in the filled configuration. It will be appreciated that the fluid may be injected into the integrated bladder 62 before or after the upper and lower jaws 52, 56 are approximated over tissue. To fill the integrated bladder 62 after the upper and lower jaws 52, 56 are approximated over tissue, the fluid may be injected through injection port 68 or 69 (FIG. 1) which may be disposed outside of the body cavity of a patient and connected to bladders 62, 64 via a delivery tube (not explicitly shown).

As detailed above, the unfilled and filled configurations were detailed with respect to the integrated bladder 62 of the lower jaw 52. It will be appreciated that the integrated bladder 64 of the upper jaw 56 has unfilled and filled configurations substantially similar to the integrated bladder 64. As such, the unfilled and filled configurations of the integrated bladder 64 will not be discussed in detail for reasons of brevity.

Figure 6:
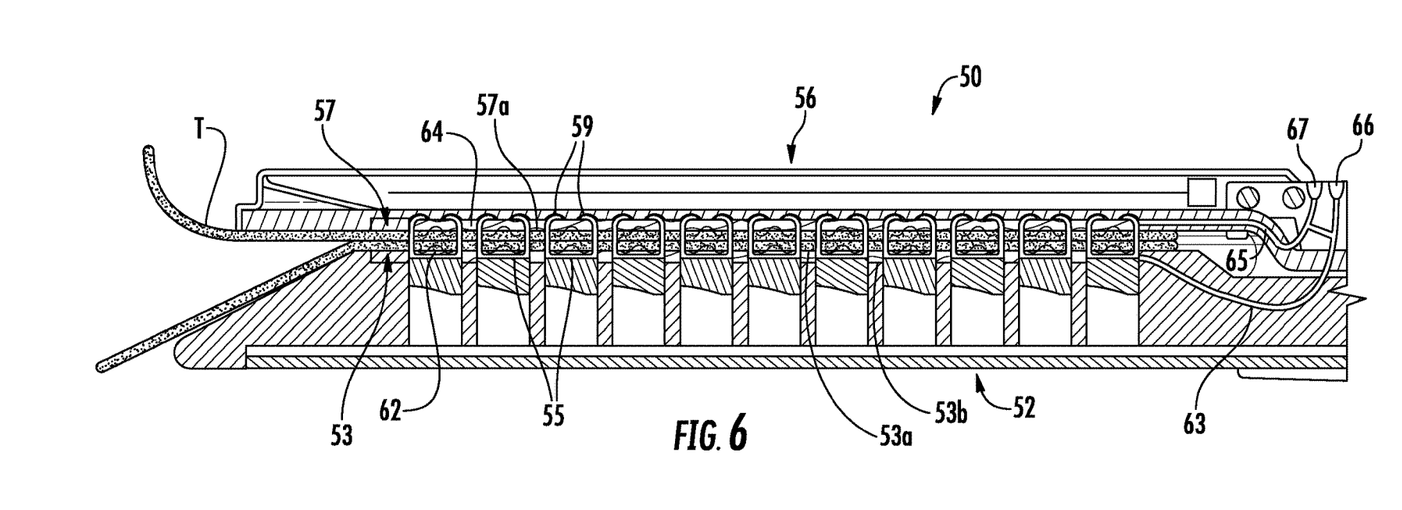
FIG. 6 is a cross-sectional view of the end effector of FIG. 5 with fasteners ejected from the lower jaw to form staples.

With reference to FIG. 6, as the fasteners 55 are ejected from the lower jaw 52 towards the upper jaw 56, the fasteners 55 pierce the integrated bladder 62 of the lower jaw 52 such that the fasteners 53 are coated with the fluid disposed within the integrated bladder 62. The coated fasteners 55 then pass through tissue T positioned between the upper and lower jaws 52, 56. After the fasteners 55 pass through the tissue T, the fasteners 55 pierce the integrated bladder 64 of the upper jaw 56 before engaging staple pockets 59 or retainers (not shown) to secure the tissue T together.

When the integrated bladders 62, 64 are pierced, the fluid from the integrated bladders 62, 64 may coat the fasteners 55 and/or the tissue T between the upper and lower jaws 52, 56. The fluid may also flow into openings in the tissue T created by the fasteners 55 to enhance anastomosis, to enhance adhesion, or to seal the tissue T to prevent bleeding of the tissue T.

Figure 7:
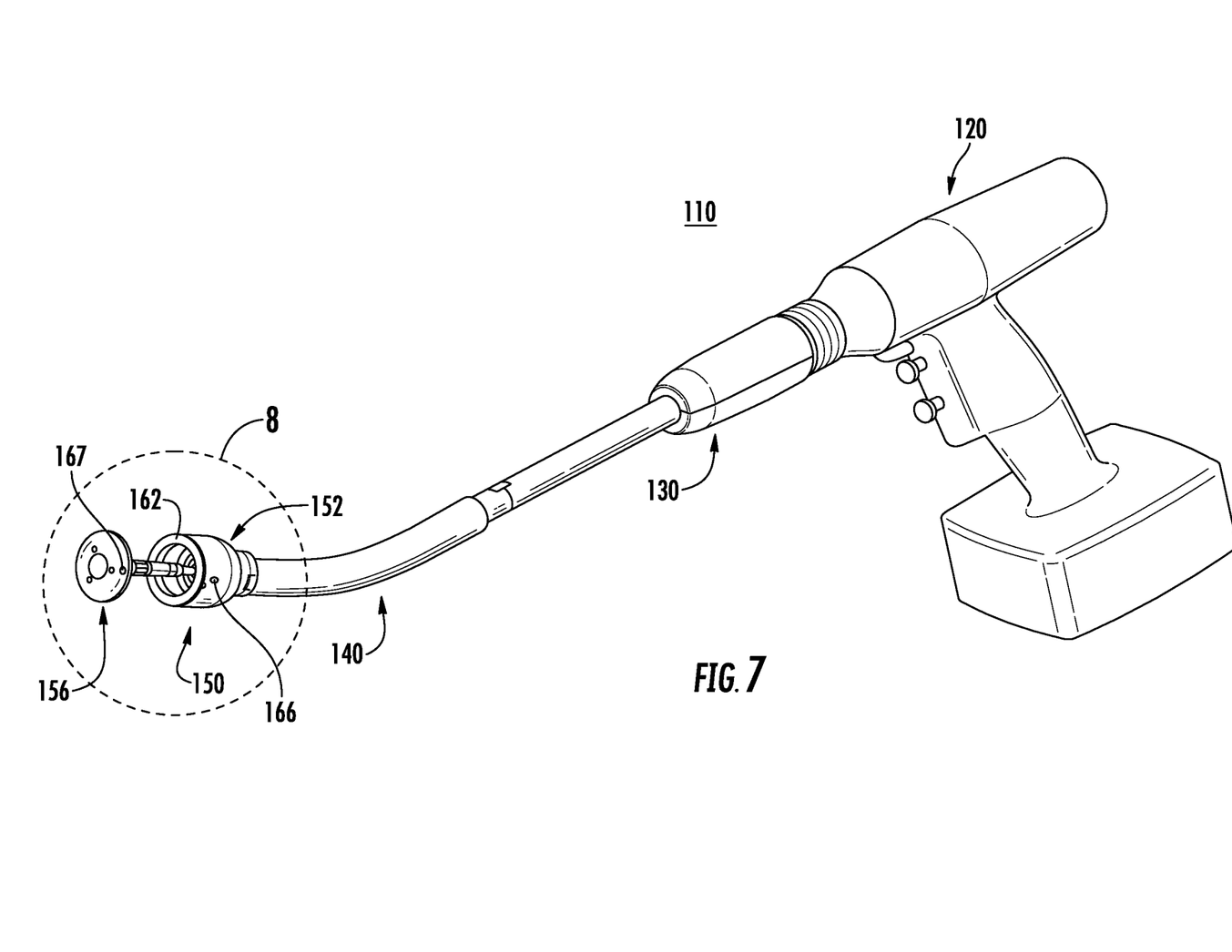
FIG. 7 is a perspective view of a surgical instrument with a powered handle and a annular stapling end effector in accordance with another exemplary embodiment of the present disclosure.

Referring now to FIG. 7, a surgical instrument 110 having a powered handle 120 including an annular or circular stapling end effector 150 is provided in accordance with another exemplary embodiment of the present disclosure. The surgical instrument 110 includes a powered handle 120, an adapter 130, a loading unit 140, and an end effector 150. The adapter 130 is releasably coupled to the powered handle 120 and extends from the powered handle 120. The loading unit 140 is releasably coupled to a distal end of the adapter 130. The end effector 150 is supported at a distal end of the loading unit 140 and includes a shell assembly 152 and an anvil assembly 156 that are moveable relative to one another. The powered handle 120 is configured to actuate the end effector 150 to approximate the shell and anvil assemblies 152, 156 of the end effector 150 relative to one another and to fire a plurality of fasteners (e.g., staples) through tissue positioned between the shell and anvil assemblies 152, 156. For a detailed description of the structure and function of an exemplary adapter and loading unit, please refer to commonly owned U.S. Provisional Patent Application Ser. No. 62/066,518 filed Oct. 21, 2014. For a detailed description of the structure and function of an exemplary powered handle, please refer to commonly owned U.S. Patent Publication No. 2012/0253329. Each of these applications is incorporated herein by reference in its entirety.

Figure 8:
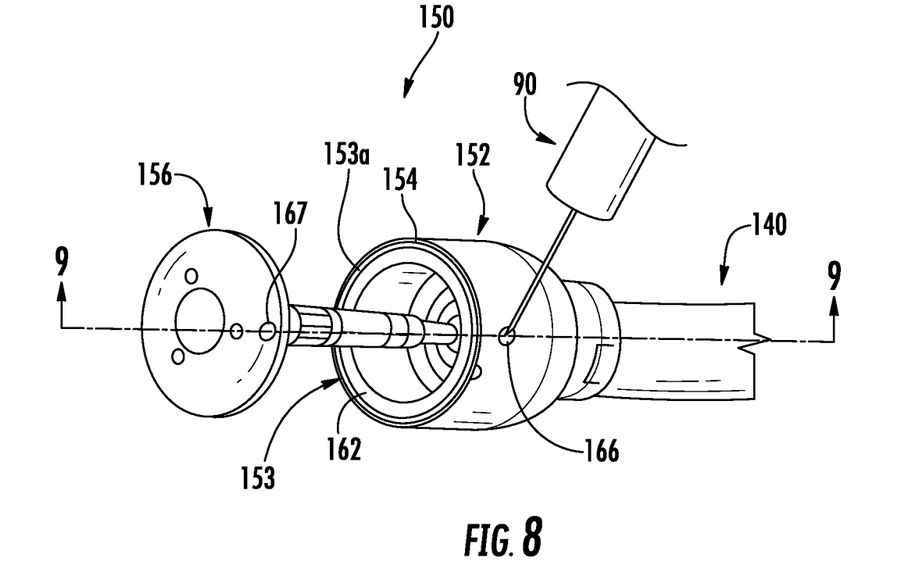
FIG. 8 is an enlarged view of the indicated area of detail of FIG. 7 with an injection device inserted into an injection port of the end effector.
Figure 9:
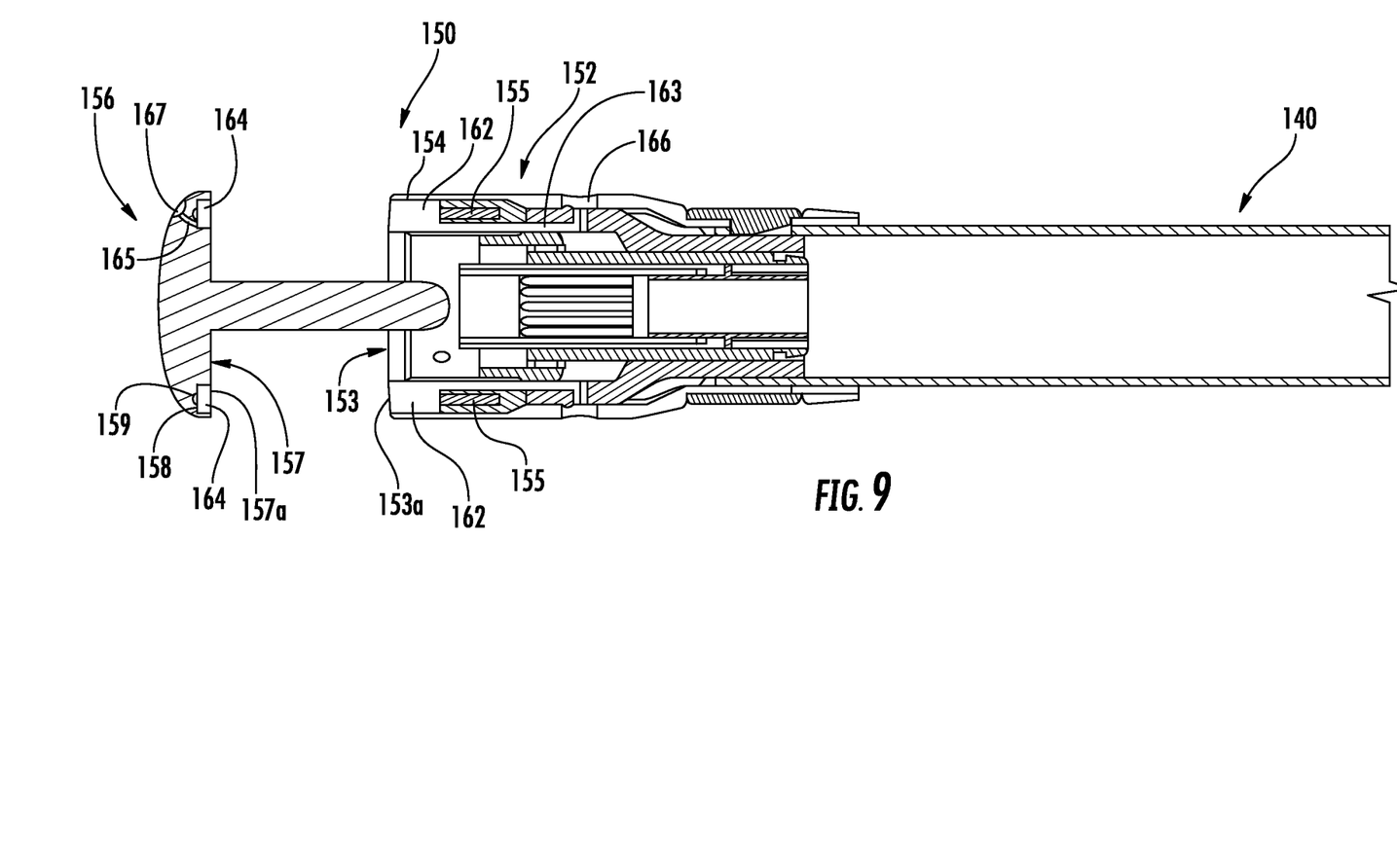
FIG. 9 is a cross-sectional view taken along the section line 9-9 of FIG. 8.

With reference to FIGS. 8 and 9, the first or shell assembly or member 152 has a tissue contacting surface 153 that defines an annular groove 154 with an outer surface of the shell assembly 152. The shell assembly 152 includes an integrated bladder 162 disposed within the annular groove 154 and positioned between a plurality of fasteners 155 and the tissue contacting surface 153. The integrated bladder 162 is defined between an outer film 153*a* disposed along the tissue contacting surface 153 and an inner film 153*b* disposed over the plurality of fasteners 155. The shell assembly 152 defines an injection port 166 that is in fluid communication with the integrated bladder 162 via a delivery tube 163.

Additionally or alternatively, the anvil assembly 156 has a tissue contacting surface 157 defines an annular groove 158. The annular groove 158 is positioned between the tissue contacting surface 157 and staple pockets 159 or retainers (not shown) of the anvil assembly 156. The anvil assembly 156 includes an integrated bladder 164 disposed within the annular groove 158. The integrated bladder 164 is defined between an outer film 157*a* and the staple pockets 159. The distal surface of the anvil assembly 156 may define a second injection port 167 that is in fluid communication with the integrated bladder 164 via a delivery tube 165.

Figure 10:
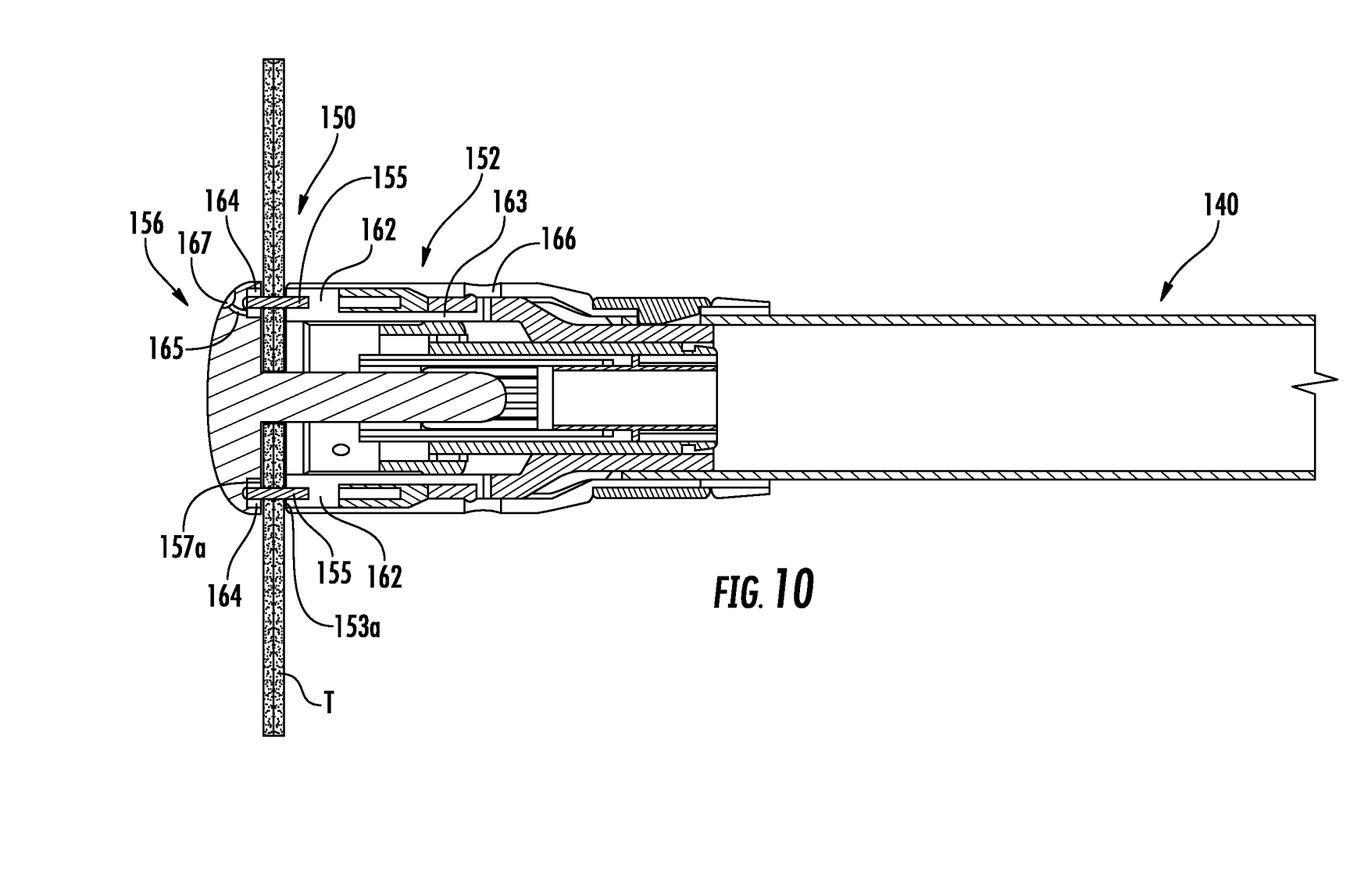
FIG. 10 is a cross-sectional view of the end effector of FIG. 9 with the anvil assembly actuated over tissue and fasteners ejected from the shell assembly towards the anvil assembly.

With reference to FIGS. 8-10, the integrated bladders 162, 164 have an unfilled configuration (FIG. 9) and a filled configuration (FIG. 10) which are substantially similar to the unfilled and filled configurations of the integrated bladders 62, 64 detailed above. As shown, the integrated bladders 162, 164 have semi-rigid walls; however, it is contemplated that integrated bladders 162, 164 may have collapsible walls as detailed above with respect to integrated bladders 62, 64.

With reference to FIG. 10 and similar to the integrated bladders 62, 64 as detailed above with respect to the linear end effector 50, the integrated bladders 162, 164 of the circular end effector 150 coat the fasteners 155 and the tissue T as the fasteners 155 are driven through the integrated bladder 162 of the shell assembly 152 to pierce the integrated bladder 162 and to secrete fluid from the integrated bladder 164 of the anvil assembly 156 as the fasteners 155 pierce the integrated bladder 164.

In any of the embodiments disclosed herein, the instrument could have channels for conveying the fluid. In such embodiments, the channels would dispense the fluid whether or not the buttress was present.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An end effector comprising:
   first and second members each having a tissue contacting surface, the first and second members movable relative to one another and configured to clamp tissue therebetween in an approximated configuration, the tissue contacting surface of the first member defining a first groove; and
   a bladder configured to receive and retain fluid, the bladder including a first film disposed along a surface of the first groove of the first member and a second film disposed on the tissue contacting surface of the first member such that sidewalls of the first groove of the first member form sidewalls of the bladder, whereby the fluid received in the bladder is exposed to the sidewalls of the first groove of the first member;
   wherein in an unfilled state the second film is positioned below the tissue contacting surface of the first member, and in the filled state the second film is coplanar with the tissue contacting surface of the first member.

2. The end effector according to claim 1, wherein the bladder is configured to receive fluid when the first and second members are in the approximated configuration.

3. The end effector according to claim 1, further comprising an injection port in fluid communication with the bladder.

4. The end effector according to claim 3, wherein the injection port is located on one of the first or second members and is configured to receive fluid from an injection device while the first and second members are in the approximated configuration.

5. The end effector according to claim 1, wherein the first member includes a fastener configured to pierce the bladder as the fastener is ejected from the first member.

6. The end effector according to claim 5, wherein the bladder is configured to dispense fluid onto tissue adjacent with the tissue contacting surface of the first member when the fastener pierces the bladder.

7. The end effector according to claim 1, wherein the tissue contacting surface of the second member defines a second groove.

8. The end effector according to claim 7, further comprising a second bladder including a third film disposed along an inner surface of the second groove and a fourth film disposed on the tissue contacting surface of the second member.

9. The end effector according to claim 1, wherein the end effector is an annular end effector, the first member is a shell assembly, and the second member is an anvil assembly.

10. The end effector according to claim 1, wherein the end effector is a linear end effector, the first member is a lower jaw, and the second member is an upper jaw.

11. A method of joining tissue comprising:
    approximating first and second members of an end effector to clamp tissue to be joined between the first and second members;
    injecting fluid into a bladder defined in one of the first or second members before or after the first and second members are clamped on tissue, the bladder defined between a first film disposed in a groove of one of the first or second members and a second film on a tissue contacting surface of the same one of the first or second members such that sidewalls of the groove of the one of the first or second members form sidewalls of the bladder, whereby a fluid received in the bladder is exposed to the sidewalls of the groove of the one of the first or second members;

wherein in an unfilled state the second film is positioned below the tissue contacting surface of the first member, and in a filled state the second film is coplanar with the tissue contacting surface of the first member; and ejecting a fastener from the first member such that the fastener pierces the bladder to release fluid from the bladder.

12. The method according to claim 11, wherein ejecting the fastener from the first member includes the fastener piercing the bladder before the fastener passes through the tissue to be joined and coating the fastener with fluid disposed within the bladder.

13. The method according to claim 11, wherein ejecting the fastener from the first member includes the fastener piercing the bladder after the fastener passes through the tissue to be joined such that the bladder secretes fluid on tissue adjacent a tissue contacting surface of the second member.

14. The method according to claim 11, wherein injecting fluid into a bladder includes injecting fluid that includes at least one of a therapeutic drug, a biocompatible adhesive, or a biocompatible sealant.

15. The method according to claim 11, wherein injecting fluid into a bladder includes injecting a first fluid into a bladder defined by the first member and injecting a second fluid into a bladder defined by the second member.

16. The method according to claim 15, wherein the second fluid is different from the first fluid.

17. The end effector according to claim 1, wherein the first member includes a fastener configured to pierce the first and second films as the fastener is ejected from the first member.

18. The end effector according to claim 17, wherein the fastener pierces the first film prior to piercing the second film.

19. The method according to claim 11, wherein ejecting the fastener from the first member includes the fastener piercing the first film prior to piercing the second film.

* * * * *